United States Patent [19]
Dean

[11] Patent Number: 5,811,394
[45] Date of Patent: *Sep. 22, 1998

[54] TECHNETIUM-99M LABELED POLYPEPTIDES FOR IMAGING

[75] Inventor: Richard T. Dean, Bedford, N.H.

[73] Assignee: Diatide, Inc., Londonderry, N.H.

[*] Notice: The term of this patent shall not extend beyond the expiration date of Pat. No. 5,654,273.

[21] Appl. No.: 480,551

[22] Filed: Jun. 7, 1995

Related U.S. Application Data

[60] Continuation of Ser. No. 264,176, Jun. 22, 1994, abandoned, which is a division of Ser. No. 653,012, Feb. 8, 1991, abandoned.

[51] Int. Cl.$^6$ .............................. A61K 38/00; C07K 5/00; C07K 7/00
[52] U.S. Cl. .............................. 514/12; 514/13; 514/14; 514/15; 514/16; 514/17; 530/324; 530/325; 530/326; 530/327; 530/328; 530/329; 530/330; 530/331; 530/300
[58] Field of Search .............................. 514/12, 13, 14, 514/15, 16, 17, 18; 530/300, 304, 324, 325, 326, 327, 328, 329, 330, 331, 391.3, 391.5, 402; 424/1.1, 2

[56] References Cited

U.S. PATENT DOCUMENTS

| | | |
|---|---|---|
| 4,434,151 | 2/1984 | Byrne et al. . |
| 4,444,690 | 4/1984 | Fritzberg et al. . |
| 4,472,509 | 9/1984 | Gansow et al. . |
| 4,571,430 | 2/1986 | Byrne et al. . |
| 4,575,556 | 3/1986 | Byrne et al. . |
| 4,578,079 | 3/1986 | Ruoslahti et al. . |
| 4,792,525 | 12/1988 | Ruoslahti et al. . |
| 4,857,508 | 8/1989 | Adams et al. . |
| 4,861,869 | 8/1989 | Nicolotti et al. . |
| 4,986,979 | 1/1991 | Morgan et al. . |
| 5,086,069 | 2/1992 | Klein et al. .............................. 514/399 |

FOREIGN PATENT DOCUMENTS

| | | |
|---|---|---|
| 135160 | 3/1985 | European Pat. Off. . |
| 84109831 | 3/1985 | European Pat. Off. ...................... 49/2 |
| 86100360 | 7/1986 | European Pat. Off. .................. 153/23 |
| 188256 | 10/1986 | European Pat. Off. . |
| 284071 | 9/1988 | European Pat. Off. . |
| 88104755 | 9/1988 | European Pat. Off. . |
| 0 301 458 A2 | 1/1989 | European Pat. Off. . |
| 398143 | 11/1990 | European Pat. Off. . |
| 0 410 537 A1 | 1/1991 | European Pat. Off. . |
| 0 410 539 A1 | 1/1991 | European Pat. Off. . |
| 0 410 540 A1 | 1/1991 | European Pat. Off. . |
| 0 410 541 A1 | 1/1991 | European Pat. Off. . |
| 0 422 937 A1 | 4/1991 | European Pat. Off. . |
| 0 422 938 A1 | 4/1991 | European Pat. Off. . |
| 0 425 212 A2 | 5/1991 | European Pat. Off. . |
| 0 478 328 A1 | 4/1992 | European Pat. Off. . |
| WO 89/05150 | 6/1989 | WIPO . |
| WO 90/10463 | 9/1990 | WIPO . |
| WO 90/15818 | 12/1990 | WIPO . |
| WO 91/01331 | 2/1991 | WIPO . |
| WO 91/15515 | 10/1991 | WIPO . |
| WO 91/17173 | 11/1991 | WIPO . |

OTHER PUBLICATIONS

Rhodes, 1974, "Considerations in the Radiolabeling of Albumin", *Sem. Nucl. Med.* 4: 281–293.

Davidson et al., 1981, "A New Class of Oxotechnetium(5+) Chelate Complexes containing a $TcON_2S_2$ Core", *Inorg. Chem.* 20: 1629–1632.

Fritzberg et al., 1982, "Synthesis and Biological Evaluation of Tc–99m N,N'–bis(mercaptoacetyl)–2,3–diaminopropanoate: A Potential Replacement for [$^{131}$I]o–iodohippurate", *J. Nucl. Med.* 23: 592–598.

Fritzberg et al., 1982, "Clinical Comparison of Tc–99m N,N'–bis(mercaptoacetamido)ethylenediamine and ($^{131}$I)ortho–iodohippurate for evaluation of renal tubular function: Concise Communication", *J. Nucl. Med.* 23: P17.

Khaw et al., 1982, "Technetium–99m Labeling of Antibodies to Cardiac Myosin Fab and to Human Fibrinogen", *J. Nucl. Med.* 23: 1011–1019.

Byrne and Tolman, 1983, "Technetium–99m Bifunctional Chelating Agent—Thiolactone for Coupling to Biomolecules, $N_2S_2$ Ligand for Chelation to Technetium", *J. Nucl. Med.* 24: P126.

Bryson et al., 1988, "Neutral Technetium(V) Complexes with Amide–Thiol–Thioether Chelating Ligands", *Inorg. Chem.* 27: 2154–2161.

Bryson et al, 1990, "Protecting Groups inb the Preparation of Thiolate Complexes of Technetium", *Inorg. Chem.* 29: 2948–2951.

Knight et al., 1990, "Thrombus Imaging with Tc–99m Synthetic peptides Reactive with Activated Platelets", *J. Nucl. Med.* 31: 757 #209.

Deuel et al., 1977, Proc. Natl. Acad. Sci. USA 74: 2256–2258 disclose the amino acid sequence of human platelet factor 4.

Niedel and Cuatrecasas, 1980, *Formyl Peptide Chemotactic Receptors of Leukocytes and Macrophages*, in Curr. Top. Cell. Reg. 17: 137–170 disclose that formyl–methionyl–leucyl–phenylalanyl peptides cause superoxide release from neutrophils.

Deuel et al., 1981, Proc. Natl. Acad. Sci. USA 78: 4584–4587 disclose that platelet factor 4 is chemotactic for neutrophils and monocytes in vitro.

(List continued on next page.)

*Primary Examiner*—Avis M. Davenport
*Attorney, Agent, or Firm*—McDonnell Boehnen Hulbert & Berghoff

[57] ABSTRACT

The invention relates to radiolabeled imaging of a mammalian body. The invention in particular provides for reagents labeled with technetium-99m for such imaging. The invention provides peptides which bind technetium-99m and which can be targeted to specific sites within a mammalian body.

6 Claims, No Drawings

OTHER PUBLICATIONS

Zoghbi et al., 1981, J. Nucl. Med. 22: 32 (Abst) disclose formyl peptide chemotactic factors (fMLF) derived from bacteria coupled to $^{111}$In–labeled transferrin.

Jiang et al., 1982, Nuklearmedizin 21: 110–113 disclose a chemotactic formylated peptide (fMLF) radiolabeled with $^{125}$I.

Osterman et al., 1982, Biochem. Biophys. Res. Comm. 107: 130–135 disclose that the carboxyl–terminal tridecapeptide of platelet factor 4 has chemotactic properties.

Holt & Niewiarowski, 1985, Sem. Hematol. 22: 151–163 provide a review of the biochemistry of platelet α–granule proteins, including platelet factor 4.

Goldman et al., 1985, Immunol. 54: 163–171 reveal that fMLF receptor–mediated uptake is inhibited in human neutrophils by platelet factor 4 and a carboxyl–terminal dodecapeptide thereof.

Loscalzo et al., 1985, Arch. Biochem. Biophys. 240: 446–455 describe the biochemical interaction between platelet factor 4 and glycosaminoglycans such as heparin.

Bebawy et al., 1986, J. Leukocyte Biol. 39: 423–434 describe the platelet factor 4–mediated chemotactic response of neutrophils in vitro.

Wilkinson, 1988, Meth. Enzymol. 162: 127–132 discloses a method for characterizing chemotactic peptides capable of causing leukocytes to move up a peptide concentration gradient.

Vorne et al., 1989, J. Nucl. Med. 30: 1332–1336 disclose the use of Tc–99m labeled leukocytes for imaging sites of infection.

LaMuraglia et al., 1989, J. Vasc Surg. 10: 20–28 disclose the use of $^{111}$In–labeled non–specific human immunoglobulin to detect sites of inflammation in vivo.

Maione et al., 1989, Science 247: 77–79 disclose that angiogenesis is inhibited by recombinant human platelet factor 4 and peptide fragments thereof.

Lind et al., 1990, J. Nucl. Med. 31: 417–473 disclose the use of Tc–99m labeled antigranulocyte monoclonal antibodies to detect inflammation.

Fischman et al., 1991, J. Nucl. Med. 32: 482–491 relates to chemotactic formyl peptide (fMLF)—$^{111}$In–labeled DTPA conjugates.

Hartman et al., 1992, "Non–peptide fibrinogen receptor antagonists: 1. Discovery and design of exosite inhibitors", J. Med. Chem. 35: 4640–4642.

Ojima et al., 1992, "Design and Synthesis of New RGD Peptides as Inhibitors of Human Platelet Aggregation", 204th Meeting, Amer. Chem. Soc. Abst. 44.

Knight, 1990, "Radiopharmaceuticals for Thrombus Detection", Sem. Nucl. Med. 20: 52–67.

Plow et al., 1987, in *Perspectives in Inflammation, Neoplasia and Vascular Cell Biology*, pp. 267–275.

Bryson et al., Inorg. Chem. 27: 2154–2161 (1988).

Bryson et al., Inorg. Chem. 29: 2948–2951 (1990).

Knight et al., Journal of Nuclear Medicine 31: 757 #209 (1990).

Rhodes, B.A., Sem. Nucl. Med. 4: 281 (1974).

Davidson et al., Inorg. Chem. 20: 1629 (1981).

Fritzberg et al., J. Nucl. Med. 23: P17 (1982).

Fritzberg et al., J. Nucl. Med. 23: 592 (1982).

Khaw et al., J. Nucl. Med. 23: 1011 (1982).

Byrne and Tolman, J. Nucl. Med. 24: P126 (1983).

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Tyr Arg Ala Leu Val Asp Thr Leu Lys
1               5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Arg Ala Leu Val Asp Thr Leu Lys
1               5

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Arg Ala Leu Val Asp Thr Leu Lys Phe Val Thr Gln Ala Glu Gly Ala
1               5                   10                  15

Lys ( 2 ) INFORMATION FOR SEQ ID NO:4:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Tyr Ala Lys Phe Arg Glu Thr Leu Glu Asp Thr Arg Asp Arg Met Tyr
1               5                   10                  15

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Ala  Lys  Phe  Arg  Glu  Thr  Leu  Glu  Asp  Thr  Arg  Asp  Arg  Met  Tyr
1                  5                        10                       15
```

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Tyr  Ala  Ala  Leu  Asp  Leu  Asn  Ala  Val  Ala  Asn  Lys  Ile  Ala  Asp  Phe
1                  5                        10                       15
Glu  Leu
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Ala  Ala  Leu  Asp  Leu  Asn  Ala  Val  Ala  Asn  Lys  Ile  Ala  Asp  Phe  Glu
1                  5                        10                       15
Leu
```

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Tyr  Arg  Ala  Leu  Val  Asp  Thr  Leu  Lys  Phe  Val  Thr  Glu  Gln  Ala  Lys
1                  5                        10                       15
Gly  Ala
```

( 2 ) INFORMATION FOR SEQ ID NO:9:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Arg  Ala  Leu  Val  Asp  Thr  Leu  Lys  Phe  Val  Thr  Glu  Gln  Ala  Lys  Gly
1                  5                        10                       15
```

Ala (2) INFORMATION FOR SEQ ID NO:10:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:10:

```
Tyr Arg Ala Leu Val Asp Thr Glu Phe Lys Val Lys Gln Glu Ala Gly
 1               5                  10                  15
Ala Lys
```

(2) INFORMATION FOR SEQ ID NO:11:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:11:

```
Arg Ala Leu Val Asp Thr Glu Phe Lys Val Lys Gln Glu Ala Gly Ala
 1               5                  10                  15
Lys
```

(2) INFORMATION FOR SEQ ID NO:12:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:12:

```
Tyr Arg Ala Leu Val Asp Thr Leu Lys Phe Val Thr Gln Ala Glu Gly
 1               5                  10                  15
Ala Lys
```

(2) INFORMATION FOR SEQ ID NO:13:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:13:

```
Val Gly Val Ala Pro Gly Val Gly Val Ala Pro Gly Val Gly Val Ala
 1               5                  10                  15
Pro Gly
```

(2) INFORMATION FOR SEQ ID NO:14:

(i) SEQUENCE CHARACTERISTICS:
        (A) LENGTH: 20 amino acids
        (B) TYPE: amino acid
        (D) TOPOLOGY: linear (ii) MOLECULE TYPE: peptide ( x i ) SEQUENCE DESCRIPTION: SEQ ID NO:14:

Val Pro Gly Val Gly Val Pro Gly Val Gly Val Pro Gly Val Gly Val
1               5                   10                  15

Pro Gly Val Gly
            20

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=formyl-Nle
            / note= "Amino terminal formyl norleucine residue"

( i x ) FEATURE:
        ( A ) NAME/KEY: Modified-site
        ( B ) LOCATION: 4
        ( D ) OTHER INFORMATION: /label=Nleu
            / note= "Norleucine residue"

( x i ) SEQUENCE DESCRIPTION: SEQ ID NO:15:

Xaa Leu Phe Xaa Tyr Lys
1               5

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=formyl-M
            / note= "Amino terminal formyl-methionine residue"

( x i ) SEQUENCE DESCRIPTION: SEQ ID NO:16:

Met Ile Phe Leu
1

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=formyl-M
            / note= "Amino terminal formyl methionine residue"

( x i ) SEQUENCE DESCRIPTION: SEQ ID NO:17:

Met Leu Phe Lys
1

( 2 ) INFORMATION FOR SEQ ID NO:18:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=formyl-M
        / note= "Amino terminal formyl methionine residue"

( x i ) SEQUENCE DESCRIPTION: SEQ ID NO:18:

Met Leu Phe Ile
1

( 2 ) INFORMATION FOR SEQ ID NO:19:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=formyl-M
        / note= "Amino terminal formyl methionine residue"

( x i ) SEQUENCE DESCRIPTION: SEQ ID NO:19:

Met Phe Ile Leu
1

( 2 ) INFORMATION FOR SEQ ID NO:20:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=formyl-M
        / note= "Amino terminal formyl methionine residue"

( x i ) SEQUENCE DESCRIPTION: SEQ ID NO:20:

Met Phe Leu Ile
1

( 2 ) INFORMATION FOR SEQ ID NO:21:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=formyl-M
        / note= "Amino terminal formyl methionine residue"

( x i ) SEQUENCE DESCRIPTION: SEQ ID NO:21:

Met Leu Ile Phe ( 2 ) INFORMATION FOR SEQ ID NO:22:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=formyl-M
            / note= "Amino terminal formyl methionine residue"

( x i ) SEQUENCE DESCRIPTION: SEQ ID NO:22:

Met Ile Leu Phe
    1

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Thr Lys Pro Arg
    1

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Val Gly Val Ala Pro Gly
    1                      5

( 2 ) INFORMATION FOR SEQ ID NO:25:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

Met Leu Phe
    1

( 2 ) INFORMATION FOR SEQ ID NO:26:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

Asn Asp Gly Asp Phe Glu Glu Ile Pro Glu Glu Tyr Leu Gln
1               5                   10

( 2 ) INFORMATION FOR SEQ ID NO:27:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 12
        ( D ) OTHER INFORMATION: /label=Tyrosine-SO3-Na
            / note= "The tyrosine derivative at this position
            has been substituted at the phenolic hydroxyl with
            sodium sulfate"

( x i ) SEQUENCE DESCRIPTION: SEQ ID NO:27:

Asn Asp Gly Asp Phe Glu Glu Ile Pro Glu Glu Tyr Leu Gln
1               5                   10

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

Gly Pro Arg Gly
1

( 2 ) INFORMATION FOR SEQ ID NO:29:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label= D- Phe
            / note= "The amino terminal phenylalanine residue
            is in the D stereochemical configuration"

( x i ) SEQUENCE DESCRIPTION: SEQ ID NO:29:

Phe Pro Arg Pro Gly Gly Gly Gly Asn Gly Asp Phe Glu Glu Ile Pro
1               5                   10                  15

Glu Glu Tyr Leu
            20

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

Arg Arg Arg Arg Arg Arg Arg Arg Arg Gly Asp Val
1               5                   10

( 2 ) INFORMATION FOR SEQ ID NO:31:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

```
Pro Leu Tyr Lys Lys Ile Ile Lys Lys Leu Leu Glu Ser
 1               5                   10
```

( 2 ) INFORMATION FOR SEQ ID NO:32:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

```
Arg Gly Asp
 1
```

( 2 ) INFORMATION FOR SEQ ID NO:33:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

```
Arg Gly Asp Ser
 1
```

( 2 ) INFORMATION FOR SEQ ID NO:34:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

```
Tyr Ile Gly Ser Arg
 1               5
```

( 2 ) INFORMATION FOR SEQ ID NO:35:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /label=Cys-S-CH2-CO-
            / note= "The side-chain sulfur atom of the carboxyl
            terminal cysteine residue is carbomethoxylated and
            esterified to the amino group of the amino ( x i ) SEQUENCE DESCRIPTION: SEQ ID NO:35:

```
Tyr  Ile  Gly  Ser  Arg  Cys
1                    5
```

( 2 ) INFORMATION FOR SEQ ID NO:36:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

```
Glu  Lys  Pro  Leu  Gln  Asn  Phe  Thr  Leu  Ser  Phe  Arg
1                    5                        10
```

( 2 ) INFORMATION FOR SEQ ID NO:37:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Cys-Acm
            / note= "This cysteine residue is protected by
            esterification with acetic a..."

( i x ) FEATURE:
        ( A ) NAME/KEY: Modified-site
        ( B ) LOCATION: 3
        ( D ) OTHER INFORMATION: /label=Cys-Acm
            / note= "This cysteine residue is protected by
            esterification with acetic a..."

( x i ) SEQUENCE DESCRIPTION: SEQ ID NO:37:

```
Cys  Gly  Cys  Gly  Gly  Arg  Gly  Asp  Ser
1                    5
```

TECHNETIUM-99M LABELED POLYPEPTIDES FOR IMAGING

This application is a continuation of application Ser. No. 08/264,176, filed Jun. 22, 1994, which was a divisional application Ser. No. 07/653,012, filed Feb. 8, 1991 both now abandoned.

BACKGROUND OF THE INVENTION

1. Field of the Invention

This invention relates to radiodiagnostic reagents and, more particularly, to polypeptides useful for producing technetium (Tc-99m) labeled radiodiagnostic agents. The invention relates to Tc-99m labeled reagents, kits for making such reagents, and methods for using such reagents.

2. Description of the Prior Art

U.S. Pat. No. 4,861,869 (Nicolotti) describes coupling agents of the formula:

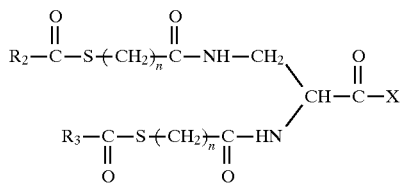

wherein $R_2$ and $R_3$ are the same or different and each represents a radical selected from the group consisting of alkyls having from 1 to 6 carbon atoms, aryls having from 6 to 8 carbon atoms and aklaryls having 7 to 9 carbon atoms, any of which can be substituted with one or more hydroxyl, alkoxy, carboxy or sulfonate groups; n is either 1 or 2; and X is an activating group capable of forming an amide bond with an alpha or beta amino group of a biologically useful protein or polypeptide molecule.

U.S. Pat. No. 4,861,869 also describes compounds such as S-benzoylmercaptoacetylglyclglyclglycine.

The coupling agents are bound to large peptides such as antibodies or fragments thereof and complexed to Tc-99m.

U.S. Pat. Nos. 4,571,430, 4,575,556 and 4,434,151 (Byrne et al.) describe compounds of the formula:

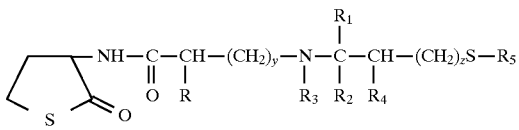

wherein R is hydrogen or lower alkyl, $R_1$ and $R_2$ are individually hydrogen or lower alkyl or taken together form oxo; $R_3$ is an amino protecting group where $R_1$ and $R_2$ taken together form oxo; $R_4$ is hydrogen or lower alkyl; $R_5$ is hydrogen or a thiol protecting group; and y and z are integers from 0 to 2; which are bifunctional chelating agents and as such can couple radionuclides to terminal amino-containing compounds capable of localizing in an organ or tissue which is desired to be imaged.

Bryson et al., *Inorg. Chem.* 27:2154–2161 (1988) and *Inorg. Chem.* 29:2948–2951 (1990), describes thiolate ligands for complexing with technetium of the formula:

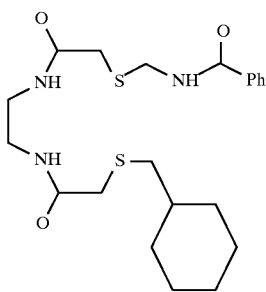

European Patent Application No. 86100360.6, filed Jan. 13, 1986, describes dithio, diamino, or diamidocarboxylic acids or amine complexes useful for making technetium imaging agents.

Other references of interest include Khaw et al., *J. Nucl. Med.* 23:1011 (1982); Rhodes, B. A., *Sem. Nucl. Med.* 4:281 (1974); Davidson et al., *Inorg. Chem.* 20:1629 (1981); and Byrne and Tolman, *J. Nucl. Med.* 24:126 (1983). See particularly Fritzberg et al., *J. Nucl. Med.* 23:592 (1982); Fritzberg et al., ibid. 23:17 (1982), for descriptions of mercaptoacetyl derivatives of ethylene diamine carboxylic acid derivates. See also U.S. Pat. Nos. 4,434,151, 4,444,690 and 4,472,509.

European Patent Application 88104755.9 describes various S-protected mercaptoacetylglycylglycine chelating groups bound to large proteins such as antibodies.

European Patent Application 84109831.2 describes technetium complexes of compounds of the formula I and II:

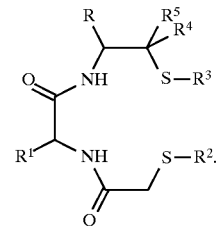

and

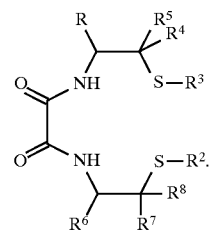

wherein R and $R_6$ are each selected from hydrogen, substituted or unsubstituted lower alkyl or —COR where $R_9$ is selected from hydroxy, substituted or unsubstituted lower alkoxy, substituted or unsubstituted amino, glycine ester, or an activated leaving group; $R_1$ is selected from hydrogen, or substituted or unsubstituted lower alkyl; $R_2$ and $R_3$ are each selected from hydrogen or a thiol protecting group; and $R_4$, $R_5$, $R_7$, and $R_8$ are each selected from hydrogen or lower alkyl; and salts thereof. These complexes were used primarily as renal function monitoring agents.

Arginylglycylaspartate (Arg—Gly—Asp or RGD) and derivative peptides are known to bind to blood clots (see U.S. Pat. Nos. 4,792,525, 4,857,508 and 4,578,079) and RGD derivatives have been labeled with technetium as imaging agents, *Journal of Nuclear Medicine* 31, pp. 757, No. 209 (1990).

SUMMARY OF THE INVENTION

The invention encompasses polypeptides for labeling with technetium-99m and imaging target sites within a mammalian body comprising (a) a specific binding polypeptide region which specifically binds to the target site to be imaged, and (b) a technetium binding region of the formula Cp(aa)Cp wherein Cp is a protected cysteine and (aa) is an amino acid and wherein the technetium binding region is covalently bound to the specific binding polypeptide region. The invention includes technetium-99m complexes and methods for using the technetium-99m complexes to image target sites within a mammalian body.

DETAILED DESCRIPTION OF THE INVENTION

The Cp(aa)Cp technetium binding group is covalently linked to the specific binding polypeptide preferably by one or more amino acids, most preferably glycine. Alternatively, the Cp(aa)Cp technetium binding group may be directly covalently linked to the specific binding polypeptide or other covalent linking groups can be used such as bifunctional amino/carboxy compounds which are not naturally-occurring amino acids.

Representative specific binding polypeptide sequences are:
Artherosclerotic Plaque Binding Peptides
YRALVDTLK (SEQ ID NO: 1)
RALVDTLK (SEQ ID NO: 2)
RALVDTLKFVTQAEGAK (SEQ ID NO: 3)
YAKFRETLEDTRDRMY (SEQ ID NO: 4)
AKFRETLEDTRDRMY (SEQ ID NO: 5)
YAALDLNAVANKIADFEL (SEQ ID NO: 6)
AALDLNAVANKIADFEL (SEQ ID NO: 7)
YRALVDTLKFVTEQAKGA (SEQ ID NO: 8)
RALVDTLKFVTEQAKGA (SEQ ID NO: 9)
YRALVDTEFKVKQEAGAK (SEQ ID NO: 10)
RALVDTEFKVKQEAGAK (SEQ ID NO: 11)
YRALVDTLKFVTQAEGAK (SEQ ID NO: 12)
Peptides Targeted to Infections and Atherosclerotic Plaque
VGVAPGVGVAPGVGVAPG (SEQ ID NO. 13)
VPGVGVPGVGVPGVGVPGVG (SEQ ID NO. 14)
formyl.Nleu.LF.Nleu.YK (SEQ ID NO. 15)
formyl MIFL (SEQ ID NO. 16)
formyl MLFK (SEQ ID NO. 17)
formyl MLFI (SEQ ID NO. 18)
formyl MFIL (SEQ ID NO. 19)
formyl MFLI (SEQ ID NO. 20)
formyl MLIF (SEQ ID NO. 21)
formyl MILF (SEQ ID NO. 22)
TKPR (SEQ ID NO. 23)
VGVAPG (SEQ ID NO. 24)
formyl MLF (SEQ ID NO. 25)
Thrombus
NDGDFEEIPEEYLQ (SEQ ID NO. 26)
NDGDFEEIPEEY(SO$_3$Na)LQ (SEQ ID NO. 27)
GPRG (SEQ ID NO. 28)
Platelets
D-Phe.PRPGGGGNGDFEEIPEEYL (SEQ ID NO. 29)
RRRRRRRRRGDV (SEQ ID NO. 30)
PLYKKIIKKLLES (SEQ ID NO. 31)
RGD (SEQ ID NO. 32)
RGDS (SEQ ID NO. 33)
Infection and Atherosclerotic Plaque
YIGSR (SEQ ID NO. 34)
CH$_2$CO.YIGSRC (SEQ ID NO. 35)
Alzheimers Disease (Amyloid Plaque)
EKPLQNFTLSFR (SEQ ID NO. 36)
[Single letter abbreviations for amino acids can be found in G. Zubay, *Biochemistry* (2nd ed.), 1988, (MacMillan Publishing: New York), p.33.]

In the Cp(aa)Cp, the Cp is a protected cysteine where the S-protecting groups are the same or different and may be but not limited to:
—CH$_2$-aryl (aryl is phenyl or alkyl or alkyloxy substituted phenyl);
—CH—(aryl)$_2$, (aryl is phenyl or alkyl or alkyloxy substituted phenyl);
—C—(aryl)$_3$, (aryl is phenyl or alkyl or alkyloxy substituted phenyl);
—CH$_2$-(4-methoxyphenyl);
—CH—(4-pyridyl)(phenyl)$_2$;
—C(CH$_3$)$_3$
—9-phenylfluorenyl;
—CH$_2$NHCOR (R is unsubstituted or substituted alkyl or aryl);
—CH$_2$—NHCOOR (R is unsubstituted or substituted alkyl or aryl);
—CONHR (R is unsubstituted or substituted alkyl or aryl);
—CH$_2$—S—CH$_2$-phenyl When Cp—gly—Cp is combined with technetium, the following complex with the protecting groups removed is formed:

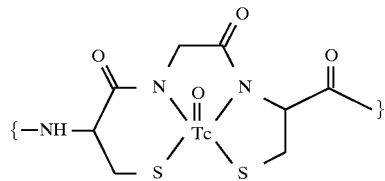

The preferred protecting group has the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl.

Compounds of the present invention can generally advantageously be prepared on an peptide synthesizer. Compounds of this invention are advantageous in that they are soluble and the sulfur is stabilized.

In forming the complex of radioactive technetium with the compounds of this invention, the technetium complex, a salt of technetium-99m pertechnetate, is reacted with the compound of this invention in the presence of a reducing agent such as stannous chloride, ferrous ion or sodium dithionite. These technetium labeled complexes can also be made by exchange of a prereduced technetium-99m complex. The complexes are conveniently provided in a kit form comprising a sealed vial containing a predetermined quantity of a compound to be labeled and a sufficient amount of reducing agent to label the compound with technetium-99m. Alternatively, the complex may be formed by reacting the compound of this invention with a pre-formed labile complex of technetium and another compound. This process is known as ligand exchange, is well known to those skilled in the art, and the labile complex may be formed using such compounds as tartrate, citrate, gluconate or mannitol, for example. Among the technetium-99m pertechnetate salts are included the alkali metal salts such as the sodium salt or ammonium salts, or lower alkyl ammonium salts. The reaction of the compound of this invention with pertechnetate or preformed labile complex can be carried out in an aqueous medium at room temperature. The anionic complex which has a charge of −1 is formed in the aqueous medium in the form of a salt with a suitable cation such as sodium, ammonium cation, mono, di- or tri-lower alkyl amine cation, etc. Any conventional salt of the anionic complex with, a pharmaceutically acceptable cation can be used in accordance with this invention.

In carrying out the reaction of the compounds of this invention with pertechnetate or a labile complex to form the anionic complex, the thiol protecting group is cleaved. Therefore, this reaction not only introduces the radioactive metal into the compound but also cleaves the thiol protecting group. All of the aforementioned thiol protecting groups are cleaved by a reaction of salts of radioactive metals in accordance with this invention.

In forming the complex the radioactive material has a suitable amount of radioactivity. In forming the Tc-99m radioactive anionic complexes, it is generally preferred to form radioactive complexes in solutions containing radioactivity at concentrations of from about 0.01 milliCuries (mCi) to 100 mCi per ml.

The complex can be used for visualizing organs such as the kidney for diagnosing disorders in these organs, tumors and blood clots can also be imaged. In accordance with this invention, the anionic complex either as a complex or as a salt with a pharmaceutically acceptable cation is administered in a single unit injectable dose. Any of the common carriers such as sterile saline solution, plasma, etc., can be utilized after the radiolabeling for preparing the injectable solution to diagnostically image various organs, clots, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 ml to about 10 ml. After intravenous administration, imaging of the organ in vivo can take place in a matter of a few minutes. However, imaging can take place, if desired, in hours or even longer, after injecting into patients. In most instances, a sufficient amount of the administered dose will accumulate in the area to be imaged within about 0.1 of an hour to permit the taking of scintiphotos. Any conventional method of imaging for diagnostic purposes can be utilized in accordance with this invention.

The complexes may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred mediums are normal saline and plasma.

The methods for making and labeling these compounds are more fully illustrated in the following examples.

EXAMPLE 1

Cys(Acm)GlyCys(Acm)GlyGlyArgGlyAspSer (SEQ ID NO. 37)

The title compound was prepared on a 0.25 millimole scale using an Applied Biosystems Model 431A peptide Synthesizer, N-terminus Fmoc protection and HMP resin (see Scheme). The product was cleaved from the resin using 95% trifluoroacetic acid at room temperature for 3 hours. Work-up and high performance liquid chromatography (HPLC) purification (using a Vydac 2.20 cm×25 cm, 10 um, C-18 column with a 20-minute gradient of 0.1% trifluoroacetic acid to 70% acetonitrile/0.1% trifluoroacetic acid at a flow rate of 25 ml/min) gave 50 mg of the title compound, 95% pure. (HPLC peak eluted at 5.5 min; Pos. ion FABMS Calc MM 952.97, Found 953).

Scheme for Preparation of the Title Compound

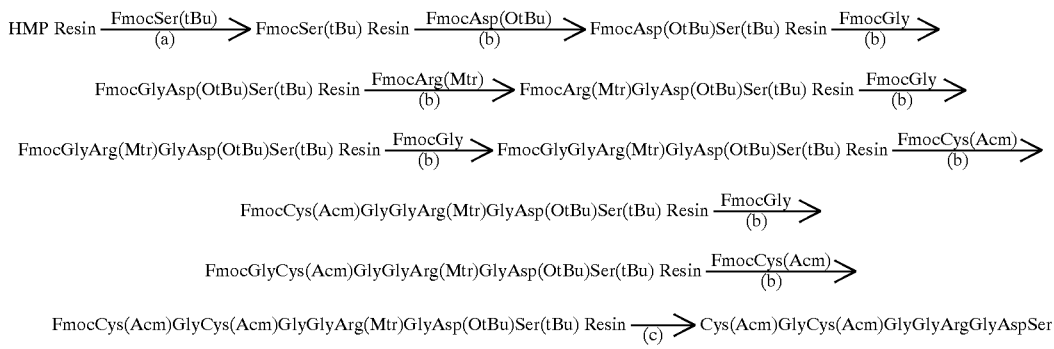

(a) DCC, HOB, NMP
(b) 1. piperidine, NMP, 2. DCC, HOB, NMP
(c) 1. piperidine, NMP, 2. 95% $CF_3CO_2H$, 3. HPLC
DCC = dcyclohexylcarbodiimide
HOB = hydroxybenztriazole
NMP = N-methylpyrrolidinone
HMP = p-hydroxymethylphenoxymethylpolystyrene
Fmoc = 9-fluorenylmethoxycarbonyl
tBu = tert-butyl
Mtr = 4-methoxy-2,3,6-trimethylbenzenesulfonyl
Acm = acetamidomethyl

EXAMPLE 2

Radiolabeling of Compound of Example 1 with Tc-99m 0.3 mg of the compound prepared as in Example 1 was dissolved in 0.3 ml of 0.05 M potassium phosphate buffer (pH 7.4) containing 0.5 mM EDTA. Tc-99m gluceptate was prepared by reconstituting a Glucoscan vial (E. I. DuPont de Nemours, Inc.) with 1.0 ml of Tc-99m sodium pertechnetate containing 26 mCi. After 15 minutes at room temperature, 75 ul of Tc-99m gluceptate was added to 0.3 mg of the compound prepared as in Example 1 and boiled for 45 minutes.

The extent of Tc-99m labeling of the peptide was determined by chomatography using Merck silica gel 60 $F_{250}$ aluminum-backed strips which were spotted with 10 ul of sample and chromatographed with acetonitrile:0.5 M sodium chloride solvent (15:85) approximately 2% of Tc-99m radioactivity remained at $R_f$ 0.0, confirming that no significant Tc-99m colloids or aggregates were generated.

The Tc-99m labeled peptide purity was determined by HPLC using a Brownlee Spheri-5 (5 um) resin, RP-18, 220×4.6 mm column and the following gradient: 0% A ($CH_3CN:H_2O:TFA$, 70:30:0.1) and 100% B (0.1% TFA in $H_2O$) to 100% A+0% B over 10 minutes at 1.5 ml/min; and then held at the 100% A solvent for 5 minutes. This protocol yielded 100% of the radiometric species detected (by in-line NaI detector) as a single species (retention time=10.9 min). Tc-99m gluceptate and Tc-99m sodium pentechnetate elute between 1 and 4 minutes under identical conditions, confirming the identity of the Tc-99m labeled peptide isolated.

What is claimed is:

1. A polypeptide reagent for preparing a scintigraphic imaging agent, the reagent comprising, in combination:

(a) a specific binding peptide that specifically binds to a target site to be imaged; and (b) a technetium binding moiety of the formula Cp(aa)Cp wherein Cp is a protected cysteine amino acid residue and (aa) is any amino acid, the technetium binding moiety being covalently bound to the specific binding peptide, and wherein the reagent has an amino acid sequence of 6 to 100 amino acids.

2. A polypeptide reagent according to claim 1 wherein the specific binding peptide and the technetium binding moiety are covalently linked through from one to about ninety amino acids.

3. A polypeptide reagent according to claim 1 wherein the sidechain sulfur atom of the cysteine residue is protected by a protecting group of the formula

—CH$_2$—NH—CO—R— wherein R is lower alkyl having 1 to 6 carbon atoms, phenyl, or phenyl substituted with lower alkyl, hydroxy, lower alkoxy, carboxy, or lower alkoxycarbonyl, or 2-pyridyl, 3-pyridyl, or 4-pyridyl.

4. A polypeptide reagent according to claim 1 wherein the Cp(aa) Cp moiety has the formula:

$$CH_2SCH_2NHCOCH_3$$
$$|$$
$$-HN-CH-CO-NH-CH_2-CO-NH-CH-CO-$$
$$|$$
$$CH_2-S-CH_2-NHCOCH_3$$

5. A polypeptide reagent according to claim 1 wherein the specific binding peptide specifically binds to clots, tumors, sites of infection, atherosclerotic plaques, amyloid plaques or bone.

6. A polypeptide reagent according to claim 1 wherein the specific binding peptide is selected from the group consisting of:

| | |
|---|---|
| YRALVDTLK | (SEQ. ID No. 1) |
| RALVDTLK | (SEQ. ID No. 2) |
| RALVDTLKFVTQAEGAK | (SEQ. ID No. 3) |
| YAKFRETLEDTRDRMY | (SEQ. ID No. 4) |
| AKFRETLEDTRDRMY | (SEQ. ID No. 5) |
| YAALDLNAVANKIADFEL | (SEQ. ID No. 6) |

-continued

| | |
|---|---|
| AALDLNAVANKIADFEL | (SEQ. ID No. 7) |
| YRALVDTLKFVTEQAKGA | (SEQ. ID No. 8) |
| RALVDTLKFVTEQAKGA | (SEQ. ID No 9) |
| YRALVDTEFKVKQEAGAK | (SEQ. ID No 10) |
| RALVSTEFKVKQEAGAK | (SEQ. ID No 11) |
| YRALVDTLKFVTQAEGAK | (SEQ. ID No 12) |
| VGVAPGVGVAPGVGVAPG | (SEQ. ID No 13) |
| VPGVGVPGVGVPGVGVPGVG | (SEQ. ID No 14) |
| formyl.Nleu.LF.Nleu.YK | (SEQ. ID No 15) |
| formyl MIFL | (SEQ. ID No 16) |
| formyl MLFK | (SEQ. ID No 17) |
| formyl MLFI | (SEQ. ID No 18) |
| formyl MFIL | (SEQ. ID No 19) |
| formyl MFLI | (SEQ. ID No 20) |
| formyl MLIF | (SEQ. ID No 21) |
| formyl MILF | (SEQ. ID No 22) |
| TKPR | (SEQ. ID No 23) |
| VGVAPG | (SEQ. ID No 24) |
| formyl MLF | (SEQ. ID No 25) |

-continued

| | |
|---|---|
| NDGDFEEIPEEYLQ | (SEQ. ID No 26) |
| NDGDFEFIPEEY($SO_3Na$)LQ | (SEQ. ID No 27) |
| GPRG | (SEQ. ID No 28) |
| D-Ohe.PRPGGGGNGDFEEIPEEYL | (SEQ. ID No 29) |
| RRRRRRRRRGDV | (SEQ. ID No 30) |
| PLYKKIIKKLLES | (SEQ. ID No 31) |
| RGD | (SEQ. ID No 32) |
| RGDS | (SEQ. ID No 33) |
| YIGSR | (SEQ. ID No 34) |
| ⁻$CH_2CO$.YIGSRC | (SEQ. ID No 35) |
| and | |
| EKPLQNFTLSFR | (SEQ. ID No 36). |

\* \* \* \* \*